(12) United States Patent
Sörlander et al.

(10) Patent No.: US 8,634,570 B2
(45) Date of Patent: Jan. 21, 2014

(54) SOUND MONITOR

(75) Inventors: Magnus Sörlander, Stockholm (SE); Tal Martin Herer, Kalix (SE); Aditya Heerah, London (GB)

(73) Assignee: Computerized Medical Technology In Sweden AB, Hållstra (SE)

( * ) Notice: Subject to any disclaimer, the term of this patent is extended or adjusted under 35 U.S.C. 154(b) by 705 days.

(21) Appl. No.: 11/884,752

(22) PCT Filed: Feb. 15, 2006

(86) PCT No.: PCT/EP2006/050965
§ 371 (c)(1),
(2), (4) Date: May 14, 2010

(87) PCT Pub. No.: WO2006/087345
PCT Pub. Date: Aug. 24, 2006

(65) Prior Publication Data
US 2010/0232615 A1 Sep. 16, 2010

Related U.S. Application Data

(60) Provisional application No. 60/597,433, filed on Dec. 1, 2005.

(30) Foreign Application Priority Data

Feb. 21, 2005 (SE) ...................................... 0500397

(51) Int. Cl.
*A61B 7/04* (2006.01)
(52) U.S. Cl.
USPC ............................... 381/67; 181/131; 600/528
(58) Field of Classification Search
USPC ........ 381/67, 56; 600/528–529, 300; 181/131
See application file for complete search history.

(56) References Cited

U.S. PATENT DOCUMENTS

| 3,562,428 | A | * | 2/1971 | Starkey et al. | .................. 381/98 |
| 4,528,689 | A | * | 7/1985 | Katz | ............................... 381/67 |
| 4,792,145 | A | | 12/1988 | Eisenberg et al. | |
| 4,903,794 | A | * | 2/1990 | Klippert et al. | ............... 181/131 |

(Continued)

FOREIGN PATENT DOCUMENTS

DE 19613261 A1 1/1997
JP 4-19881 2/1992

(Continued)

OTHER PUBLICATIONS

PCT/ISA/210—International Search Report—Jun. 6, 2007
PCT/IPEA/409—International Preliminary Report on Patentability—Jun. 6, 2007.
European Search Report—Mar. 13, 2009.

(Continued)

*Primary Examiner* — Xu Mei
(74) *Attorney, Agent, or Firm* — Venable LLP; Eric J. Franklin

(57) ABSTRACT

An electronic sound monitor for use as a stethoscope, a signal treatment and a method for treating the signals using the monitor. The sound monitor includes at least one transducer for transforming vibrations to electrical signals, a filtering, A/D- and D/A-converter, amplifier, a processor, a sound chamber in which at least one transducer for transforming electrical signals to sound is arranged, and a sound channel opening into the sound chamber. The sound channel being adapted to forward the sound from the sound chamber through an opening connecting the sound channel with the ambient air.

20 Claims, 9 Drawing Sheets

(56) References Cited

U.S. PATENT DOCUMENTS

| | | | |
|---|---|---|---|
| 4,947,859 A * | 8/1990 | Brewer et al. | 600/528 |
| 5,003,605 A * | 3/1991 | Phillipps et al. | 381/67 |
| 5,821,471 A * | 10/1998 | McCuller | 181/156 |
| 6,438,238 B1 | 8/2002 | Callahan | |
| 6,467,568 B1 * | 10/2002 | Kemper | 181/131 |
| 7,096,060 B2 * | 8/2006 | Arand et al. | 600/513 |
| 2003/0072457 A1 | 4/2003 | Grasfield et al. | |
| 2005/0014999 A1 | 1/2005 | Rahe-Meyer | |
| 2005/0107715 A1 * | 5/2005 | Abbruscato | 600/528 |

FOREIGN PATENT DOCUMENTS

| | | |
|---|---|---|
| JP | 6-217387 | 5/1994 |
| JP | 9-28702 | 2/1997 |
| JP | 10-85209 | 4/1998 |
| WO | WO 96/06562 | 3/1996 |
| WO | WO-02/32313 A1 | 4/2002 |
| WO | WO 03/011124 A2 | 2/2003 |

* cited by examiner

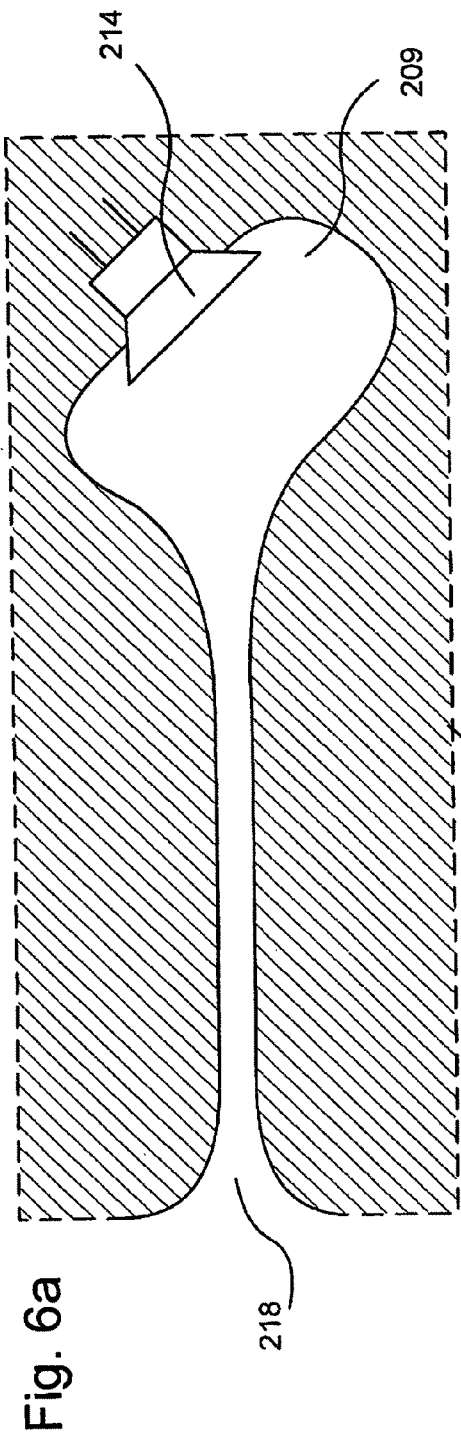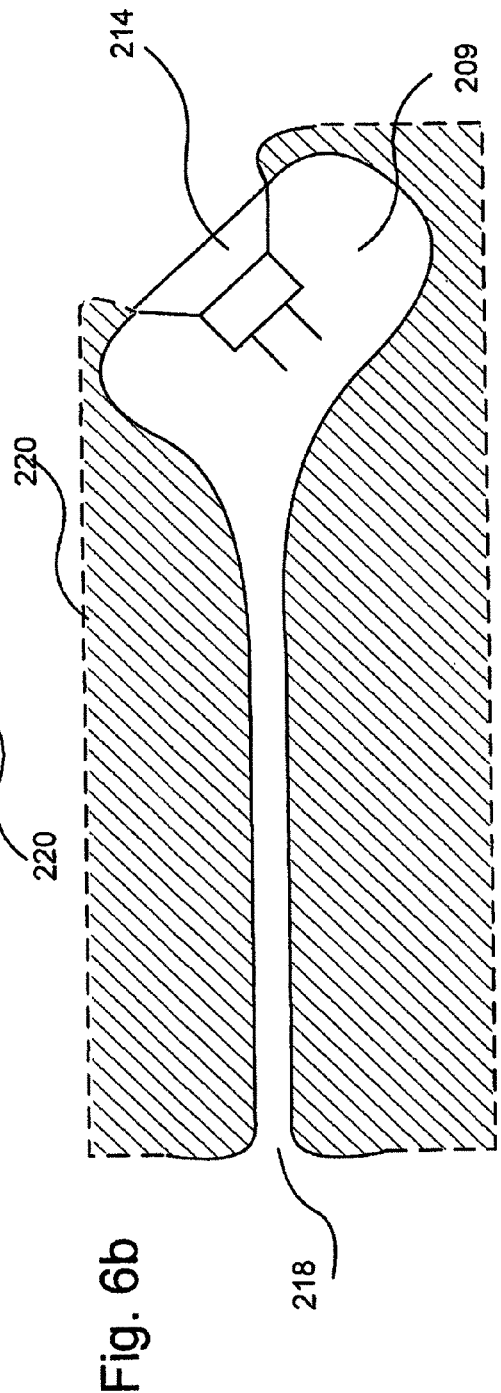

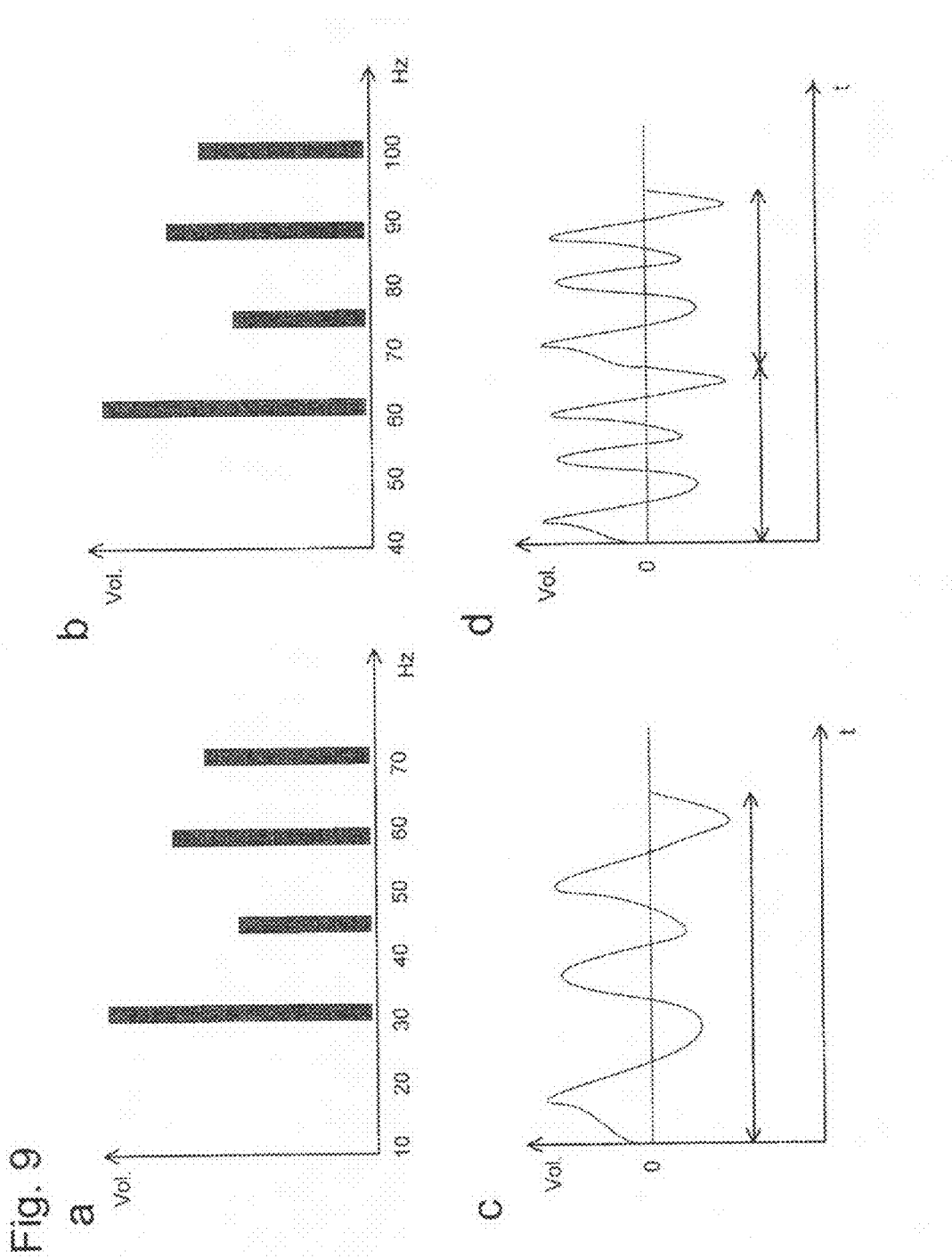

SOUND MONITOR

CROSS-REFERENCE TO RELATED APPLICATIONS

This application claims priority to U.S. provisional patent application 60/597,433 filed 1 Dec. 2005 and Swedish patent application 0500397-5 filed 21 Feb. 2005 and is the national phase under 35 U.S.C. §371 of PCT/EP2006/050965 filed 15 Feb. 2006.

FIELD OF THE INVENTION

The invention relates to a sound monitor for thoracic and abdominal organs, which is primarily intended to be used as a stethoscope.

BACKGROUND OF THE INVENTION

In the text below the invention will be referred to as a "sound monitor" in order to differentiate the invention from the common stethoscope.

Definitions used in the text and for the purpose of this invention intended to encompass the following:
"transducer for transforming vibrations to electrical signals", also called "vibration transducer" e.g. a microphone, a piezoelectric element, and a piezoelectric film.
"transducer for transforming electrical signals to sound" exemplified by e.g. a loud speaker or the equivalent.
"collecting structure" is used for the structure in which the vibration transducer is arranged, e.g. a protruding bell, open-ended, an essentially cylindrical member, or other embodiments describe in the description. The open-ended structure may be closed by a membrane or a cushion, arranged in the structure or at the open end of the same.

The commonly used acoustic stethoscope was invented in 1816 by a Doctor Laennec. The basic design has not been altered since then. The ordinary acoustic stethoscope has a membrane covered chestpiece, which is connected to a flexible tube; this tube is spilt into two parts each having an ear piece. The sound from e.g. a beating heart is captured by the chestpiece and the sound is passed on to the ears of the auscultator, i.e. generally a doctor.

In conventional practice a doctor will apply a stethoscope to a patient and arrive at a conclusion based on the sounds perceived by the doctor. To receive a second opinion, another doctor will have to be able to apply a stethoscope and hear the same sounds. This is a problem—there might not be another doctor present or the other doctor may have hearing problems or frequency response problem.

Another problem occurs in teaching when teaching the student/-s to differentiate between different sounds relating to e.g. the heart cycle only one person can listen at a time. There is no possibility of pointing out a specific sound related to a specific event in the heart.

Inherent problems with the stethoscopes of current acoustic design are thus: Unfavorable design for education, listening in is impossible for simultaneous identification of sounds, abnormalities are hard to detect and impossible to filter. Murmurs are hard to detect without amplification, filtering and isolation.

Listening in during consultation is not easy, and that patients cannot listen in, mystifies the whole process and makes communication and explanations more difficult. With an acoustic stethoscope it is virtually impossible to store sounds for later playback. A microphone and means for treating and storing the sounds are needed to this end.

In the acoustic stethoscope the sound produced by an organ of a living is picked up by a chest piece in the form of pressure waves and from there routed to a flexible acoustic tube, which continues in two acoustic conduits each ending with an ear piece. Acoustic pressure (sound waves) is transported from the chest piece through the conduits to the respective ear piece and will act on the ear to produce sound. The success of the auscultation is thus inherently dependent not only on the stethoscope but also the ears and perception of the auscultator is part of the process. The hearing in different persons naturally differ between the persons and also in the same person the hearing changes with age. Sounds which the young person easily perceives may be totally impossible for the older person to hear.

The traditionally used chest piece has a further drawback in that when the person listening to bodily sounds e.g. the heart sounds he may want to listen at several locations. The reasons may be that the sound is transplanted differently in different directions or when listening to the lungs the doctor listens normally at several quite closely place locations. This means that when the chest piece is moved it is lifted away from the body and put down at a new location. While the chest piece is lifted all sounds from the body are cut off. This gives the doctor several occasions to adjust to listening at every location as the process is broken off when chest piece is lifted.

Medical personnel learn the art of auscultation primarily through the use of an acoustic stethoscope and are trained to hear normal and abnormal heart and lung sounds based on their specific acoustic qualities and the timing relative to other biological sounds.

Electronic stethoscopes with amplification and filtering of sounds are known within the art. In such a stethoscope the sound from biological activity is picked up by a microphone and the signal may be filtered such as to remove noise etc. The filtering is also indicated as being e.g. selective in order to remove signals emanating from another organ than the one which is the focus of the investigation. The signal is thereafter sent to a loud speaker in the conduits of the stethoscope. Such a stethoscope is known from a published US patent application US 2003/0072457 (published Apr. 17, 2004).

Electronic stethoscopes comprising a handheld chest piece communicating with an ear piece or other apparatuses as loudspeakers, recording means etc are also known within the art.

Typically the prior art requires transducers capable of reproducing the full range or close to the full range of sound generated by the body organs. Heart sounds generally lie within the span 17-500 Hz. Key frequencies of interest lie within the span of 17-200 Hz, and some of the more important sounds are found between 17-70 Hz. Small loudspeakers and other transducers have difficulties reproducing this lower frequency range, thus the choice of ear pieces in the prior art is natural.

An object of the invention is an electronic stethoscope, below termed "sound monitor" or "monitor" having improved functionality and design.

A further object of the invention is to provide for an electronic sound monitor which gives the doctor an enhanced and easy to use tool in everyday practice and also during auscultations when there are several listeners.

A further object of the invention is to make possible the use of small loud speakers or other electrical to audio transducers, which are not capable of representing the frequencies generated by the organs of interest. Further objects are solved by the invention through the method devised which involves frequency manipulation of sounds to be reproduced on these devices. This same method has an additional use. In some instances a loud speaker or audio transducer can represent sounds not easily audible by the listener due to limitations of the human in general or a specific defect of the listener's hearing. This method can bring previously inaudible sound into ranges more suitable for the individual.

An example of an organ sound may be heart murmurs. These sounds may occur in addition to normal heart sounds or may even replace aspects of normal heart sounds. To detect or identify these murmurs the sounds are according to the invention altered in aspect so as to intensify the sounds of interest. Organs of the body like the heart have a predictable sequence of sounds. Methods to identify these sequences may include e.g. following selectable options of:

Removal or reduction of known normal sequences of heart sounds or other organs by the mean of analog or digitally analyzing the sound to identify and reduce sections not of interest. This feature in itself is known e.g. through WO02/32313.

Standard automatic volume control in the analog or digital domain normally described as automatic gain control (AGC). The purpose is to maintain a volume level that can be accommodated by the electronic processing methods preventing overload.

Standard filtering techniques like band-pass, hi-pass, and low-pass filters in the analog or digital domain.

Dynamic scaling of sounds in the analog or digital domain, normally described as compression techniques which limits the magnitude of signals to a given range. Lowering the volume of high level sounds and increasing the volume of lower level sounds.

Dynamic scaling of sounds in the analog or digital domain, normally described as expansion techniques which increases the magnitude of signals over a given range. Increasing the volume of higher level sounds in comparison with lower level sounds.

Further to these methods, which may be used in the monitor according to the invention there will be described below new methods according to the invention regarding the pitch of the sound.

All of the above may be used singly or in combination, selectable by the listener to most effectively target the sounds of interest. Additionally the processing methodology allows automatic adjustments of the parameters that control sound manipulation. This enables the device to maintain the most effective output, tracking changes in the nature of organ sounds.

These and other objects are attained by manipulating the sound such that the frequency is scaled such that the duration and relative sequences of the sound are retained, meaning that the timing of the sounds is correct but the frequency of the sound is different. The final output may not even include frequencies present in the original signal. The effect is that sounds effectively are lifted in pitch facilitating use of small loudspeakers. In fact the organ sounds lowest in pitch, are not possible to be heard even when large loudspeakers are used. When using small loudspeakers in apparatuses according to the art the lower pitched sounds are de facto not represented.

SUMMARY OF THE INVENTION

The present invention comprises a sound monitor for use as a stethoscope comprising at least one transducer for transforming vibrations to electrical signals, filtering means, A/D- and D/A-converter means, amplification means, processing means, a sound chamber, in which at least one transducer for transforming electrical signals to sound, is arranged, and a sound channel opening into said sound chamber, said sound channel adapted to forward the sound from the sound chamber through an opening connecting the sound channel with the ambient air.

The transducer for transforming vibrations to electrical signals is arranged in a vibration collecting structure.

A further embodiment of the invention resides in manipulating the sound picked up by the sound monitor such that the frequency is scaled such that the "information" is effectively lifted in pitch facilitating use of small loudspeakers. Examples of these are:

Pitch alteration of sounds in the analog or digital domain, whilst retaining the original output duration. Creating an effect of listening with higher or lower pitch.

Pitch alteration of sounds in the analog or digital domain, whilst altering the original output duration. This creates an effect of listening at slower speed or higher speed.

In a further embodiment according to the invention a special type of signal processing is used which will scale the information such that the timing of each sounds is virtually correct. This is done using a variety and combination of methods according to the invention to be described below.

In still a further embodiment of the invention the chest piece has no acoustic tubing for connecting the chest piece directly with any ear pieces. A power amplifier is used to drive a small speaker mounted within the device such that multiple listeners in a room may make experience the selected human organ sounds. This amplifier has considerably more power than one used to drive ear phones.

However ear pieces may still be used to connect to a common apparatus for distribution of the sounds to several listening persons. The ear pieces connected to the common apparatus may also be used in order to keep surrounding noise at a low level and thereby facilitating the perception of sounds.

BRIEF DESCRIPTION OF THE DRAWINGS

In the drawings and in which like elements have been given like reference characters:

FIG. 6 shows two embodiments according to the invention of the sound chamber, sound channel and throat.

DETAILED DESCRIPTION

Figure 1:
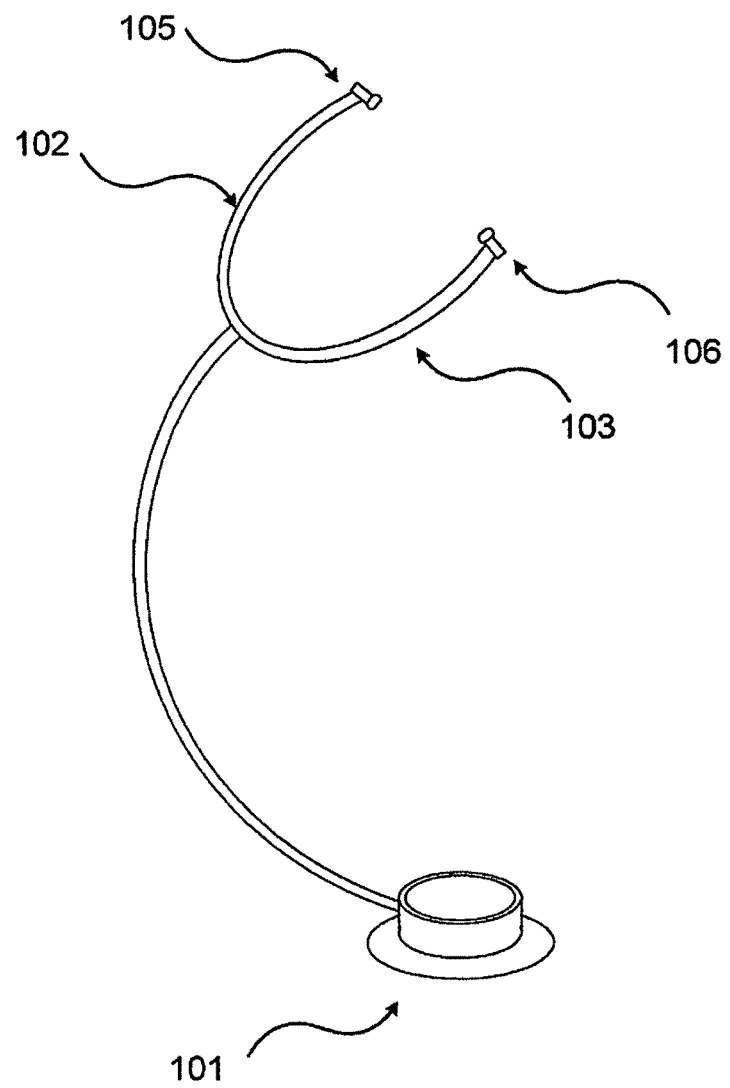
FIG. 1 shows a common stethoscope according to the prior art.

For the purpose of illustration, the present invention will now be explained with reference to a common stethoscope according to the prior art for use in listening to bodily sounds such as the sounds emanating from a human heart. Such a stethoscope is shown in FIG. 1.

In the figure is seen a chest piece 101, which is attached to a flexible acoustic tubing 102, which is divide into two binaurals 103, 104 each exhibiting an attached ear piece 105, 106. The sound is picked up by the chest piece an effectively passed as sound waves into the ear of the listener. This is a representative picture of the old type of stethoscope. In a newer type of stethoscope the sound is picked up not by the chest piece by a microphone. This microphone may be placed in a small container attached as a part of the flexible acoustic tubing e.g. where the tubing divides into the binaurals. The container may include a microphone, an amplifier and a loudspeaker. This arrangement works in the analog mode, exhibit simple filtering means and may also have a possibility of storing and replaying at half the speed.

Traditionally the doctors do not want any distortion of the sound, which has presented bars to changing the concept of the stethoscope.

Figure 2:
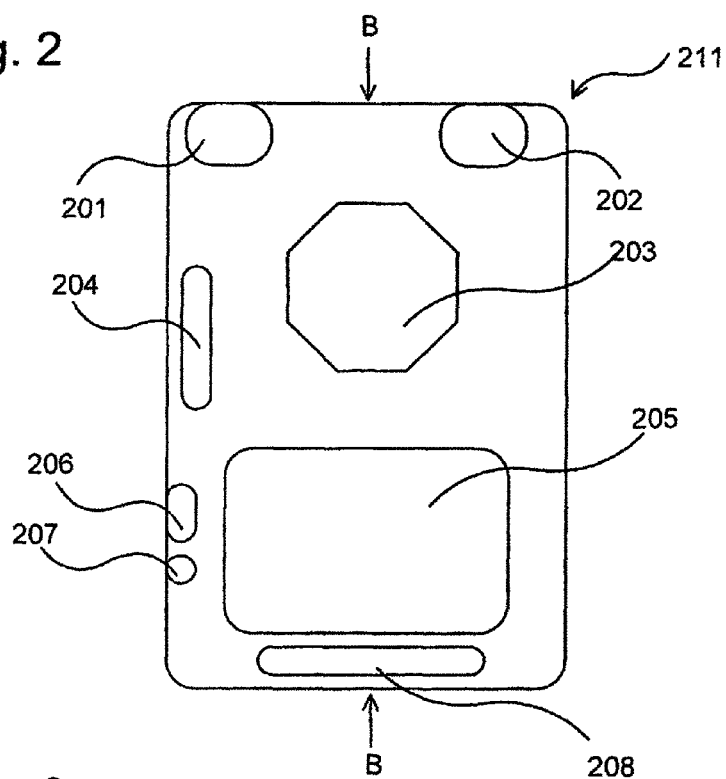
FIG. 2 shows a view of a sound monitor according to the invention.
Figure 3:
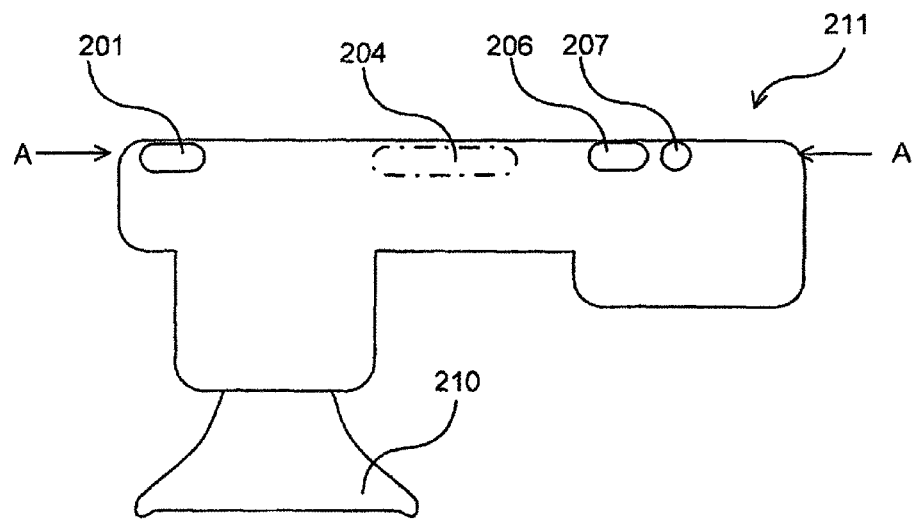
FIG. 3 shows at schematic side view of a sound monitor according to the invention.
Figure 4:
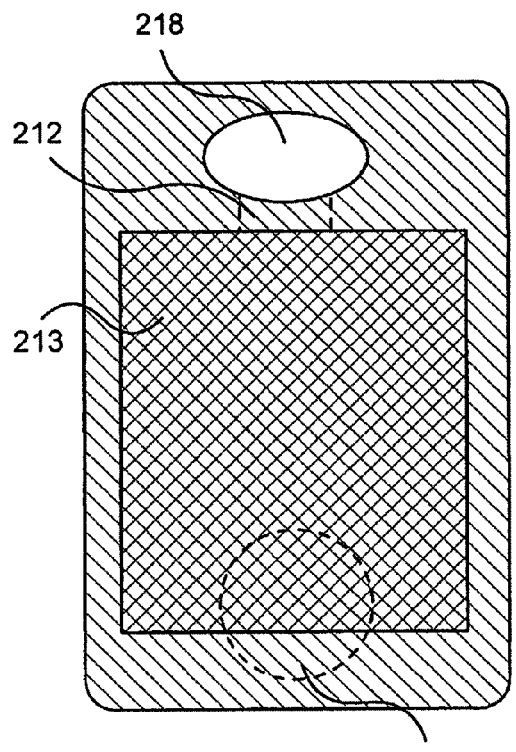
FIG. 4 shows a section of the sound monitor according to the invention along A-A indicated in FIG. 3.

According to one embodiment of the invention the sound monitor, shown in FIGS. 2-4, comprises an upper 211 and a lower part 210. Within FIGS. 2-4 the reference numbers are common for the details that are shown. The lower part 210, a vibration collecting structure, is also termed the bell. In the lower part of the bell a cushion is, in this embodiment, arranged such as to contact the body. In an alternative embodiment the bell has a further bell-shaped structure arranged inside the bell 210 in which the transducer, e.g. a microphone, is arranged. The two arrangements will be commented further below. Further embodiments are described in connection with FIG. 8.

Although the lower part above is named bell in connection with FIGS. 2-4, this lower part may in further embodiments be a protruding or built-in vibration collecting structure comprising a vibration receiving means which may be e.g. be a microphone or a piezo-electric means, for the purpose of this application termed transducers of vibrations to electrical signals.

To be noted is that lower and upper part refers to the set-up in FIG. 2 as shown. The lower part 210 comprises the vibration transducer and the collecting structure therefore.

In the described embodiment the bell-shaped lower part 210 comprises a liquid-filled cushion.

In FIG. 2a the upper part 211 of the sound monitor is shown from above. A button for start/stop listening 201, a button for start/stop recording 202, speaker outlet 203, a volume control 204, a LCD display 205, an IR port 206, a head set outlet 207, and a menu control 208 are shown. It should be understood that this is a schematic drawing and that the design of the sound monitor may be adapted such as to be easily used with one hand.

In FIG. 3 the sound monitor is seen in a side view showing the upper part 211 having a start/stop listening 201 button (the button for start/stop recording 202 not shown), the IR port 206, and a head set outlet 207.

In FIG. 4 a section parallel to the upper surface of the sound monitor approximately along the line A-A in FIG. 3 is shown. In the figure the loud speaker 214, a circuit board with CPU 213, part of the sound channel 212, and the throat 218 of the sound channel 212 are indicated.

Figure 5:
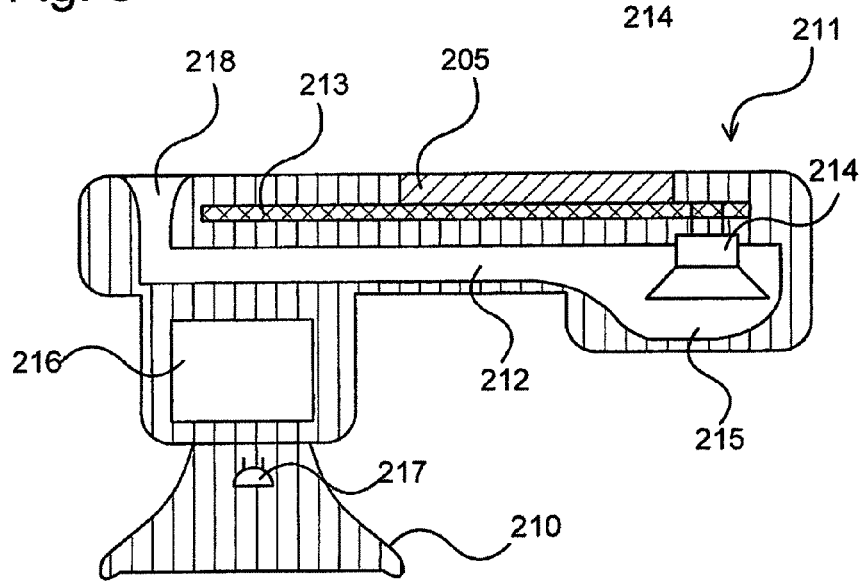
FIG. 5 shows a section of the sound monitor according to the invention along B-B indicated in FIG. 2.

In FIG. 5 a section along the line B-B in FIG. 3 is shown here in the upper part 211 are the LCD display 205, the circuit board with CPU 213, the arrangement of the sound chamber 215, the sound channel 212, and the throat 218. In the sound chamber 215 a loud speaker 214 is arranged. This arrangement will be further discussed below in connection with FIG. 6.

In the upper part (211) the channel and the chamber (215) are arranged as shown in order to enhance the lower frequencies. The lower the frequencies the longer the channel must be (compare the sizes of a base loud speaker to the size of a treble speaker. Using the channel and chamber makes sure that sound of lower frequencies are not only scaled up but also directionally focused. Sounds of low frequencies spread around whereas the higher pitched sounds are directional.

It is pointed out that in an acoustic stethoscope this problem does not exist as the sound picked up by the chest piece is directly delivered into the ear (i.e. a relatively closed space).

In conjunction with FIGS. 6a and 6b two embodiments of the arrangement of throat, channel, and chamber will be described. The preferred embodiment is the one shown in FIG. 6a. In the two figures the same reference numbers refer to the corresponding detail. The arrangement of the loudspeaker, chamber, channel and throat are critical to the performance of the device.

The physical limits of the device are schematically indicated by the dashed line 220. This is only to indicate that the entire channel 212 except the opening or throat 218 of the channel is enclosed within the device. In the opposite end of the channel 212 from the throat 218 a chamber 209 is situated. In this chamber 209 a small loudspeaker 214 is arranged for sending out the picked up sounds having undergone signal treatment in the device.

The two embodiments differ in that the throat 218 and the loudspeakers 209 are somewhat different arranged.

In the embodiment according to FIG. 6a, complete enclosure of the loudspeaker facilitates easier cleaning as there are fewer openings in the device housing. The channel design may follow curved paths in order that the overall arrangement can be accommodated within the physical dimensions of the device. The design of throat 218 uses exponential curves to form a flared horn. Here the throat, chamber, and channel combination is designed to produce a horn effect for maximum sensitivity and directionality. This arrangement thus provides the highest sound output with increased directionality.

In the embodiment according to FIG. 6b, the design employs a direct radiating loudspeaker with the throat and channel arrangement providing reinforcement of the bass frequencies. In this version the throat is narrower compared with embodiment according to FIG. 6a. The throat, chamber and channel combination is designed so that the throat output augments the output from the speaker, reinforcing the low frequencies. The direct radiating loudspeaker, radiating through an opening directly into the air gives greater dispersion of sound which may be advantageous where several listeners are involved. The sound thus comes directly from the loud speaker and also indirectly through the sound channel.

The volume control button may be maneuvered using e.g. the thumb. As shown, two buttons are arranged at the front of the upper part (one not visible, being on the back side) for use in maneuvering the listening etc. The functionality of the sound monitor may be arranged such that the auscultator holds the chest piece/sound monitor in the palm of the hand such that the loud speaker will be situated between the fingers. The thumb is used for the volume control, and the middle finger controls the off/on buttons.

As the cushion arranged at the bottom of the bell-shaped lower part 210 is placed against the body and the on/off button is pressed the device starts an "active listening", i.e. the sounds are picked up and the sounds will be heard through the loudspeaker. The active listening is aim at identifying the specific sound feature which is looked for. Once the sound has been identified/found a recording is started by pressing the recording button with the middle finger. The device is removed from the body and by once more pressing the recording button with the middle finger a repeating playback of the last recorded sound. By sound is here meant the sound over a predetermined period to be decided e.g. by the user depending on the application. For the playback the signals representing the recorded sound may be treated using filtering etc.

The cushion is preferably filled with a suitable medium. This is done in order to reduce the loss of frequency and levels during the transition of the picked up sounds between different media. In an acoustic stethoscope the sound comes from the body, the body comprising mostly fluid, is transferred through air to a pick up device (in the acoustic stethoscope there is actually no pick-up device as the sound is transferred through the tubing directly to the ear, the ear being the pick-up device According to one embodiment of the invention this is substituted by the following transitions: from the body, comprising mostly fluid, the sound is transferred through a liquid and from there to a vibration collecting structure and vibration transducer. Regarding the type of liquid in the cushion it may be a liquid having low viscosity e.g. methanol. Material having a viscosity in the higher ranges gives less noise however lower viscosity gives better amplification or rather less of the sound is lost as compared to air.

However, alternatively a high viscosity liquid or even a gel may be employed to deliberately curtail the reception of higher frequencies.

Figure 7:
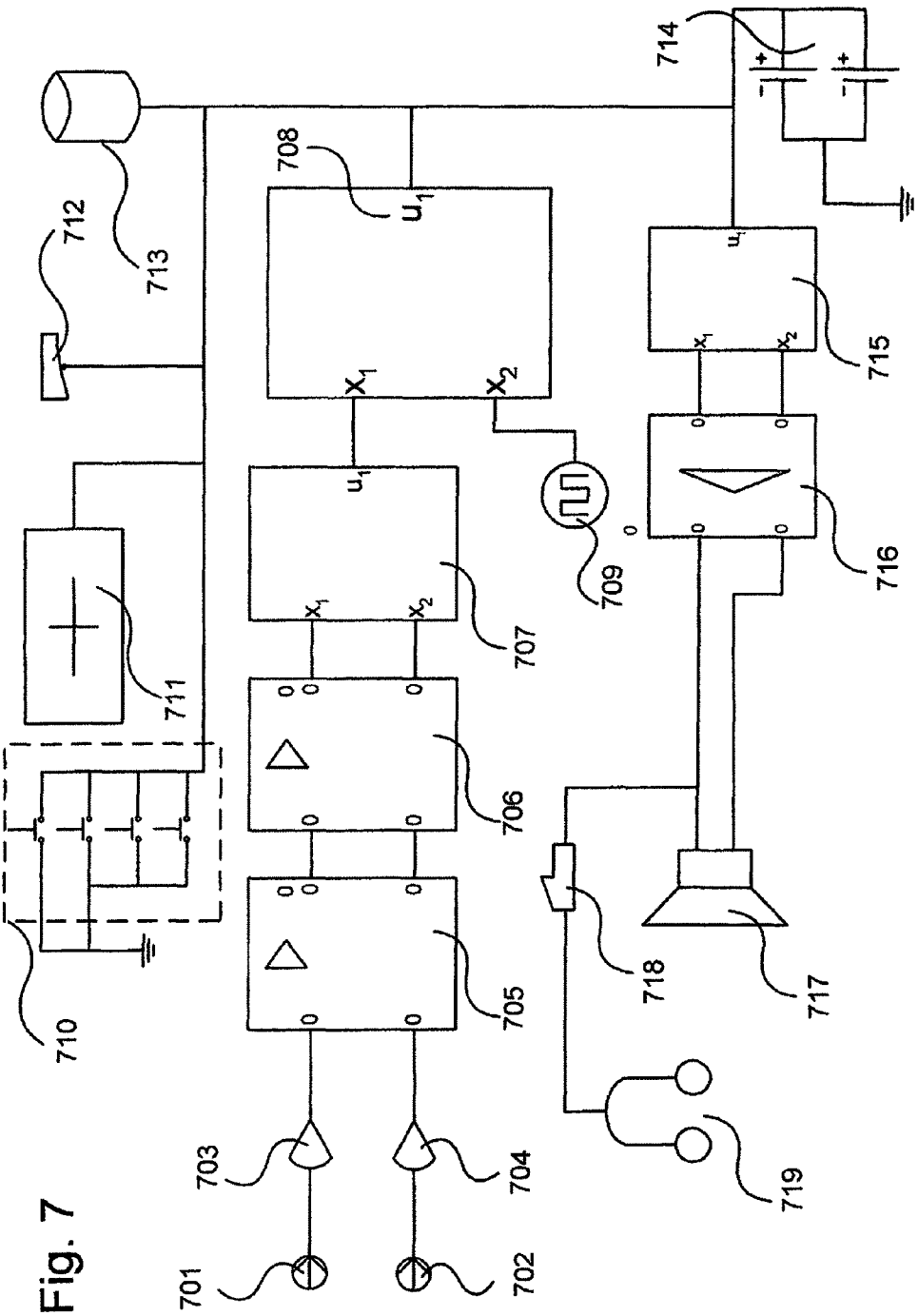
FIG. 7 is a block diagram showing one example of the device according to the invention.

An embodiment of the invention may be electrically implemented as is shown in the block diagram in FIG. 7. The vibration transducer 701 is arranged in the part of the device which is pressed against the body to pick up bodily sounds. The analog signals from the same will appear on the input of the input amplifier 703. The signals are there amplified and thereafter treated in an analog filter 705 comprising: band pass filter, high pass filter, and low pass filter. The filtered signals are applied on an analog gain amplifier 706 comprising two input gain controls, respectively. The amplified signals are then converted in a two channel A/D-converter 707 to analog signals. These analog signals are applied on the input of a digital signal processor 708. The digital signal processor 708 comprises a clock source 709.

There is also an auxiliary transducer 702 with corresponding input amplifier 704 and a corresponding signal path as clear from the above description and the diagram. There are two possible uses for the auxiliary transducer 702:
1. On a very small child or in other special cases there might be hard to reach places using the primary built in transducer. In such cases can a small external transducer connected via wire better be suited for the purpose (smaller for babies, larger for animals, special shaped or mounted for various projects)
2. An auxiliary transducer, can in especially noisy environments, be attached in order to pick up surrounding sounds. The unwanted sound can then be cancelled from the sound picked up by the primary transducer. This method of using an external microphone to pick up noise is often used on headsets in airplanes.

The digital signal processor 708 is adapted to apply the special signal treatment described below in connection with the figures On the device there are controls, here shown as a number of switches 710, which are adapted to allow option selection and parameter control for input to the digital signal processor 708 on which a program is run. There is also a LCD matrix display 711 for displaying data by the program, either showing chosen options/parameters or showing messages from the program. The LCD-display may also in one embodiment be adapted to show wave forms untreated or treated sounds.

Also arranged is a scroll control 712 for LCD menus. A solid state storage 713 for replay and analysis of captured audio data is also arranged. The device may optionally have means for e.g. IR or radio communication with an external storage device (not shown) for further storage of audio data.

Also shown is a battery power supply and voltage monitor 714 for powering the device.

The signals treated in the digital signal processor 708 according to the program run on the same and under the conditions laid down by the option selected and the chosen parameters there producing corresponding signals transformed according to the inputs. The transformed signals are then treated in a digital to analog converter 715. The output is subjected to gain control in a power amplifier 716, which may be manipulated by the user. On the output of the power amplifier a small loudspeaker, e.g. having a diameter of approx. 5 cm or less, is arranged.

An optional earphone or headphone output 718 may be arranged. Headphones 719 are shown in the drawing.

In FIG. 8 is shown further embodiments of the sound monitor according to the invention. The part of the monitor named lower part alt. bell in the foregoing may also be designed differently. The lower part will in connection with this figure be termed vibration collecting structure and this is intended to cover both the transducer for transforming vibrations to electrical signals and the structure, in which the transducer is mounted, where the structure exhibits different geometrical forms.

Figure 8A:
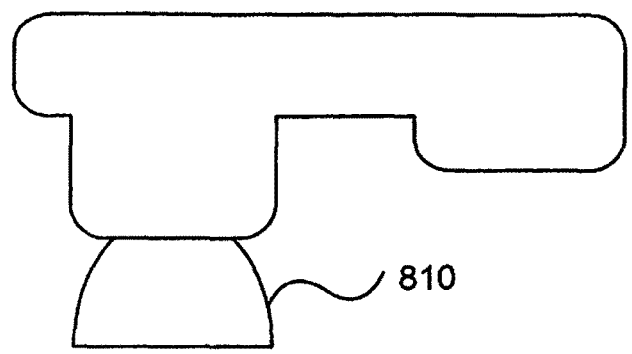
FIG. 8 show further embodiments of the vibration collecting structure of the monitor according to the invention FIG. 9 *a-h* shows methods employed according to the invention to alter the pitch of a signal whilst maintaining the original duration.

In FIG. 8a is shown an example of the "bell" which does not answer to the form of a traditional bell, rather to a bowl-like form. In this bowl the transducer is mounted.

Figure 8B:
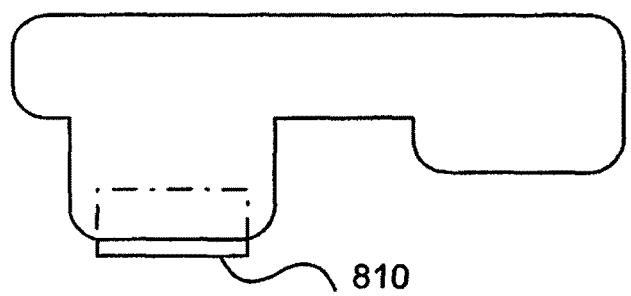
Figure 8C:
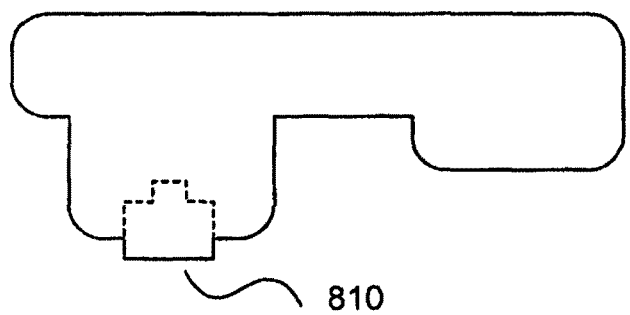
Figure 8D:
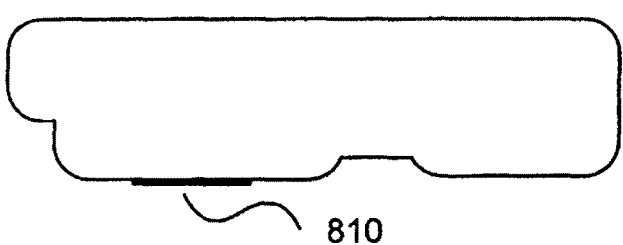
Figure 8E:

In FIG. 8b is shown an embodiment in which the vibration collecting structure is essentially built into the monitor. The structure here has a cylindrical form with either a circular or oval cross-section. FIG. 8c shows the corresponding structure as mounted on the bottom of the monitor and finally FIG. 8d illustrates the vibration collecting structure and the transducer as essentially built-in in the monitor. FIG. 8e exemplifies that the cross-section of the surrounding structure may exhibit different forms.

In this connection it is pointed out that the transducer for transforming vibrations to electrical signals may not only comprise what is normally termed as a microphone but also may consist of a piezoelectric element or a piezoelectric film which is mounted in the cylinder, surrounding structure, extended on a adapted frame member in a pre-stressed state covering essentially the cross-section of the cylinder.

In the case where a cushion is applied the piezoelectric film, said film may also be arranged on one of both sides of the cushion. The film should also here be tight and extended. In this manner the piezoelectric film will essentially be in direct contact with the skin of the patient the vibrations will be captured by the piezoelectric film and transformed into electrical signals.

The program for use in the digital signal processing of the signals according to the invention may either be a loadable software or partly implemented as hardware in the device.

According to a further embodiment of the invention a signal treatment has been devised in which the pitch of the sound is raised without changing the timescale of the sound. This is important, as the lifting up of the sounds to higher frequencies allows for using small loudspeakers, to hear sounds that would hardly be audible and by conserving the timescale of the sounds e.g. a normal heart cycle is easy to identify. The frequency shifting (scaling up) of the sound should of course be individual to the person depending among other things on the hearing of that person.

Figure 9:
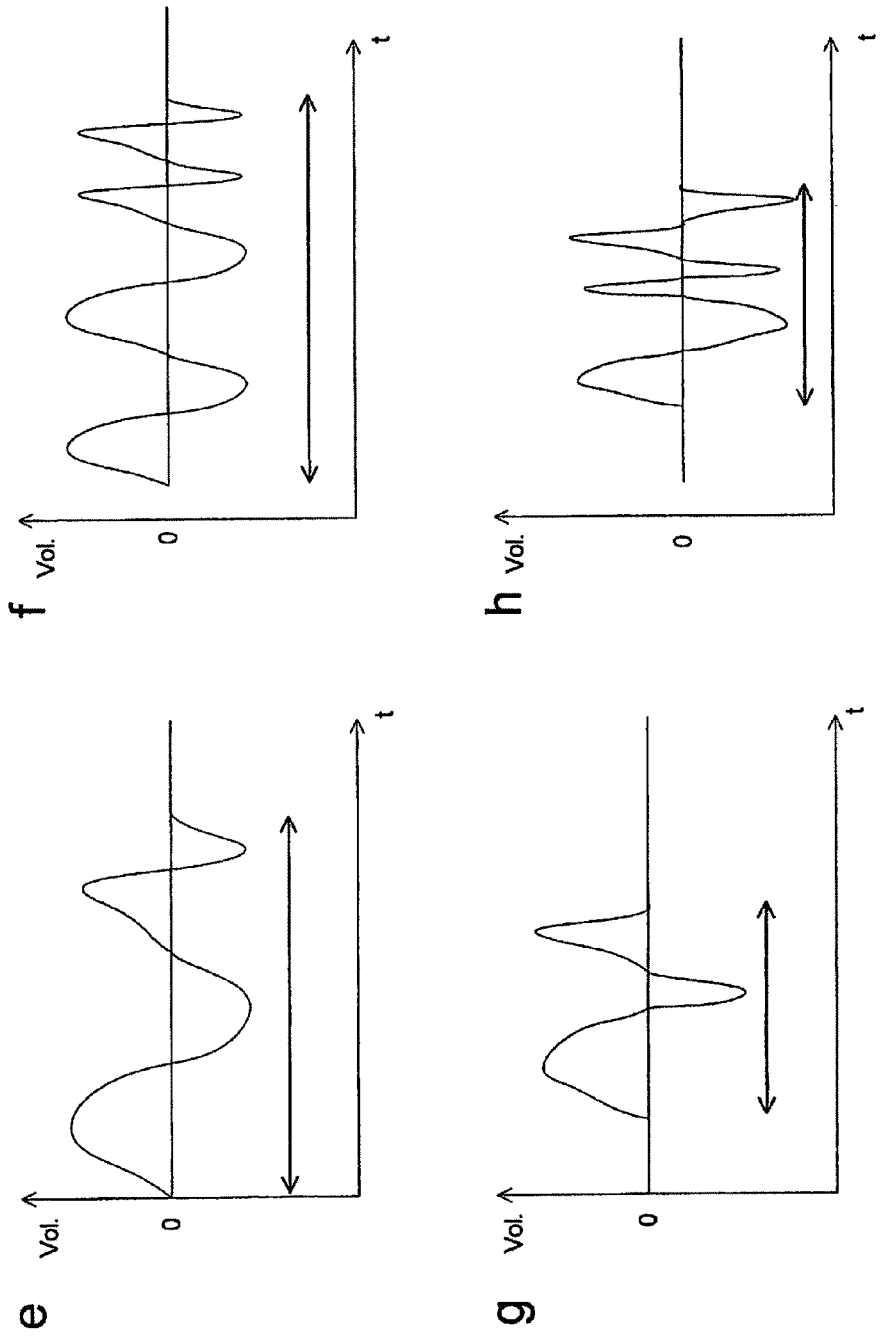

In FIG. 9a is shown a digital analysis by FFT (Fast Fourier Transform) method of a possible signal. A signal waveform may be analyzed in this manner in sections. The FFT method produces a list of the constituent frequencies, their magnitude, and relative relationship. The individual components are pure sine waves which are easy to describe mathematically, and so may be scaled to differing frequencies. These new frequencies are recombined with the same relative relationship to produce a pitch shifted version of the original as seen in FIG. 9b. As each section is analyzed and reconstituted some form of smoothing may be necessary at section boundaries. Overlap of sections followed by cross-fading when the signal is reconstituted minimizes artifacts.

A characteristic of FFT analysis is that it does require significant computing power. The device's digital signal processor may not be able to provide this level of computing on a continuous basis. Therefore other schemes are used to achieve pitch shifting which require less computational overhead.

FIGS. 9c and 9d demonstrates a scheme that requires the least computation. A window of waveform samples is replayed at double rate and replicated. When the next window is processed, cross-fading between windows minimizes artifacts.

The above method is further extended by detecting where the signal crosses the zero axis, so allowing cycles and half cycles of waveform to be identified. FIGS. 9e and 9f show how cycles may be replicated and replayed at twice speed to achieve a doubling of pitch and retention of the original duration.

FIGS. 9g and 9h show half cycle replication at twice speed. In this case the polarity of each replicated half cycle must be inverted to achieve the smoothest splice.

After the above treatments, the signal may not be represented by a smooth curve. The phenomenon is more or less severe depending on how close the sampling is done. There are also algorithms for smoothing the signal which are known in signal processing especially in the recording of music. Some of the algorithms require a resampling of the signal. This may be achieved at a mathematical level from the original data. Alternatively an additional analog to digital converter can be employed which operates at a different sampling frequency from the first. Utilization of this second converter minimizes computational overhead. This is important as some of these calculations require a lot of computational capacity and the combination of computational methods will speed up the process and save processor space.

Figure 10A:
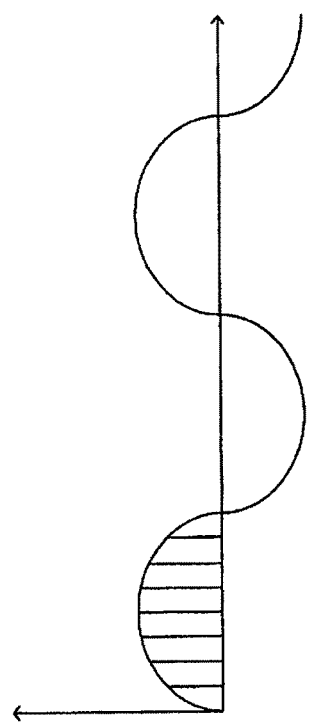
FIG. 10 *a-b* illustrates a composite signal and a corresponding signal treated in accordance with the invention, the type of "sampling" used and the reconstruction of the signal is also illustrated.
Figure 10B:
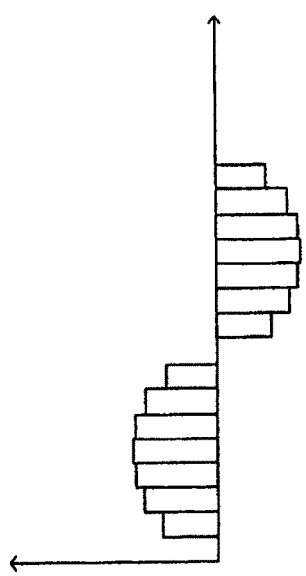

The invention allows treatment of sounds using a mix of the above processes. The type of "sampling" according to the invention is also illustrated in FIG. 10. This is exemplified in the FIG. 10a-10b. In the figures volume/magnitude of a signal is plotted as a function of time.

In FIG. 8g an original waveform is plotted and a window is indicated by a horizontal arrow. The method used is pitch shift by half cycle replication. The resulting pitch doubled waveform is shown in FIG. 8h. The equivalent time window is indicated.

The shorter the sampling period, the better result of course.

A further use of the FFT analysis technique by the device is to identify the most commonly encountered heart or other organ abnormalities.

Use of the cushion according to the invention gives the benefit of reducing external noise and removes some of the interruptions when moving the sound monitors on the body as described above. However according to a further embodiment of the inventive sound monitor the cushion may be replaced by a bell-type means. The bell will be surrounded by an outer protective shell and is resiliently suspended using threads or other flexible suspension. This has shown to give good results. The inner bell will be in contact with the skin of the patient but the fingers of the auscultator will be in contact with the outer shell of the bell. Thus no noise will be transferred to the inner device.

The invention claimed is:

1. An electronic sound monitor for use as a stethoscope, comprising:
   at least one transducer configured to transform vibrations to electrical signals,
   a directly radiating loud speaker configured to receive the electrical signals and transform the electrical signals into audible sounds and directly radiate the audible sounds to ambient air,
   a filter configured to filter the electrical signals,
   A/D- and D/A-converter configured to convert the electrical signals,
   an amplifier configured to amplify the electrical signals,
   a processor configured to alter the electrical signals to lift the pitch of the sounds and alter frequencies of the vibrations without altering a timing of the vibrations when the electrical signals are transformed into audible sounds,
   a sound chamber in which the directly radiating loudspeaker is arranged, the sound chamber comprising an opening directly to ambient air, and
   a sound channel leading to and opening into said sound chamber, said sound channel adapted to forward sound from the sound chamber through an opening connecting the sound channel with the ambient air, the sound channel comprising a throat, wherein the throat of the sound channel and the sound channel are arranged to reinforce low frequencies.

2. The electronic sound monitor according to claim 1, further comprising:
   a vibration collecting structure in which the at least one transducer for transforming vibrations to electrical signals is arranged.

3. The electronic sound monitor according to claim 2, wherein the vibration collecting structure is bell-shaped.

4. The electronic sound monitor according to claim 2, wherein the vibration collecting structure is of a generally cylindrical form.

5. The electronic sound monitor according to claim 3, further comprising:
   a cushion in which the at least one transducer for transforming vibrations to electrical signals is enclosed, the cushion being arranged within the vibration collecting structure of the monitor, said cushion being adapted to be pressed against a body of a person.

6. The electronic sound monitor according to claim 3, further comprising:
   a bell-shaped part comprising an inner bell shaped part in which the at least one transducer for transforming vibrations to electrical signals is suspended, wherein the bell-shaped part is adapted to be pressed against a body of a person.

7. The electronic sound monitor according to claim 1, wherein the sound chamber solely leads to the sound channel and the throat of the sound channel, the sound chamber, and the sound channel combination is designed to produce a horn effect.

8. The electronic sound monitor according to claim 1, wherein the throat of the sound channel is flared out and ends in an opening on the upper part of the monitor.

9. The electronic sound monitor according to claim 5, wherein the cushion is filled with a fluid having a viscosity which is in the approximate range of 0.6-1.6 cP.

10. The electronic sound monitor according to claim 5, wherein the cushion is filled with a gel having a viscosity which is in the approximate range of 40-2000 cP.

11. The electronic sound monitor according to claim 1, wherein the processor is configured to carry out computer program instructions that lift the pitch of captured sounds in an analog or digital domain, thereby retaining an original duration of the pitch altered sounds.

12. The electronic sound monitor according to claim 1, wherein the processor is configured to carry out computer program instructions that lift the pitch of captured sounds in an analog or digital domain, thereby altering an original duration of the pitch altered sounds.

13. The electronic sound monitor according to claim 1, wherein the processor is configured to carry out computer program instructions that cause a perceived pitch alteration of captured sounds in the analog or digital domain without altering an actual pitch of the captured sounds, by adjusting the relative phase of high frequency and low frequency components.

14. The electronic sound monitor according to claim 1, wherein the processor is configured to carry out computer program instructions that alter aspects of loud and quiet sounds such that the quiet sounds are not heavily masked by the loud sounds, by adjusting the relative volumes of sections occurring in rhythmic sequences.

15. The electronic sound monitor according to claim 1, wherein the processor is configured to carry out computer program instructions that identify commonly occurring rhythmic sequences from the organs of the body.

16. A method in a sound monitor of a stethoscope, comprising:
    directing sound in the stethoscope from a directly radiating loud speaker of the stethoscope into to a sound chamber of the stethoscope, through a sound channel of the stethoscope leading to and opening into the sound chamber, and from the sound chamber through an opening connecting the sound channel with ambient air, wherein the sound channel comprises a throat and an opening directly to ambient air, and wherein the throat of the sound channel and the sound channel are arranged to reinforce low frequencies,
    transforming vibrations of the sound to electrical signals in the stethoscope,
    altering in the stethoscope the electrical signals to lift a pitch of the sounds and altering frequencies of the vibrations without altering a timing of the vibrations in an analog or digital domain when the electrical signals are transformed into audible sounds,
    retaining in the stethoscope an original duration of the pitch altered sounds by multiplying sampled sounds, and
    receiving in the stethoscope the electrical signals and transforming in the stethoscope the electrical signals into audible sounds and directly radiating the audible sounds to ambient air.

17. The method according to claim 16, further comprising:
    altering in the stethoscope the original output duration of the pitch altered sounds.

18. The method according to claim 16, further comprising:
    altering in the stethoscope a perceived pitch of captured sounds in the analog or digital domain without altering in the stethoscope the actual pitch, by adjusting in the stethoscope the relative phase of high frequency and low frequency components.

19. The method according to claim 16, further comprising:
    altering in the stethoscope aspects of loud and quiet sounds of the captured sounds such that the quiet sounds are not heavily masked by the loud sounds, by adjusting in the stethoscope the relative volumes of sections occurring in rhythmic sequences.

20. The method according to claim 16, further comprising:
    identifying in the stethoscope commonly occurring rhythmic sequences from organs of a body.

* * * * *

UNITED STATES PATENT AND TRADEMARK OFFICE
CERTIFICATE OF CORRECTION

PATENT NO. : 8,634,570 B2  
APPLICATION NO. : 11/884752  
DATED : January 21, 2014  
INVENTOR(S) : Sörlander et al.

Page 1 of 1

It is certified that error appears in the above-identified patent and that said Letters Patent is hereby corrected as shown below:

On the Title Page

Under "Assignee"

Item (73) should read,

Computerized Medical Technology In Sweden ~~AG~~ AB, Hållsta, (SE)

Signed and Sealed this  
Sixteenth Day of September, 2014

Michelle K. Lee  
*Deputy Director of the United States Patent and Trademark Office*